(12) United States Patent
Ganin et al.

(10) Patent No.: US 7,518,114 B2
(45) Date of Patent: Apr. 14, 2009

(54) METHOD AND SYSTEM FOR IMAGING A PATIENT

(75) Inventors: Alexander Ganin, Whitefish Bay, WI (US); Floribertus Philippus Martinus Heukensfeldt Jansen, Ballston Lake, NY (US); Ricardo Scott Avila, Clifton Park, NY (US); Dinko Eduardo Gonzalez Trotter, Clifton Park, NY (US); Ravindra Mohan Manjeshwar, Guilderland, NY (US); James Vradenburg Miller, Clifton Park, NY (US); Thomas Baby Sebastian, Flemington, NJ (US)

(73) Assignee: General Electric Company, Schenectady, NY (US)

( * ) Notice: Subject to any disclaimer, the term of this patent is extended or adjusted under 35 U.S.C. 154(b) by 488 days.

(21) Appl. No.: 10/985,752

(22) Filed: Nov. 10, 2004

(65) Prior Publication Data

US 2006/0097175 A1 May 11, 2006

(51) Int. Cl.
*G01T 1/164* (2006.01)
*G01T 1/166* (2006.01)
(52) U.S. Cl. ............................. 250/363.03; 250/363.04
(58) Field of Classification Search ............ 250/363.01, 250/363.02, 363.03, 363.04, 363.09; 378/4, 378/5, 8, 62
See application file for complete search history.

(56) References Cited

U.S. PATENT DOCUMENTS

| 4,980,552 | A | * | 12/1990 | Cho et al. | 250/363.03 |
| 5,272,343 | A | * | 12/1993 | Stearns | 250/363.03 |
| 5,665,971 | A | * | 9/1997 | Chen et al. | 250/385.1 |
| 6,255,655 | B1 | * | 7/2001 | McCroskey et al. | 250/363.03 |
| 6,346,706 | B1 | * | 2/2002 | Rogers et al. | 250/363.04 |
| 6,490,476 | B1 | * | 12/2002 | Townsend et al. | 600/427 |
| 6,507,633 | B1 | * | 1/2003 | Elbakri et al. | 378/8 |
| 6,574,304 | B1 | | 6/2003 | Hsieh et al. | |
| 6,687,329 | B1 | | 2/2004 | Hsieh et al. | |
| 6,810,103 | B1 | * | 10/2004 | Tybinkowski et al. | 378/20 |
| 6,878,941 | B2 | * | 4/2005 | Balan et al. | 250/363.02 |
| 7,180,074 | B1 | * | 2/2007 | Crosetto | 250/370.09 |
| 2004/0195512 | A1 | * | 10/2004 | Crosetto | 250/363.04 |
| 2006/0108509 | A1 | * | 5/2006 | Frangioni et al. | 250/208.1 |
| 2007/0085013 | A1 | * | 4/2007 | Watson | 250/363.07 |
| 2008/0107229 | A1 | * | 5/2008 | Thomas et al. | 378/4 |

* cited by examiner

*Primary Examiner*—David P Porta
*Assistant Examiner*—Faye Boosalis
(74) *Attorney, Agent, or Firm*—Dean D. Small; The Small Patent Law Group LLP

(57) ABSTRACT

Methods and systems for imaging a patient are provided. The method includes determining a location of a volume of interest within the patient and acquiring a plurality of frames of emission data, at least one frame including the volume of interest. The method further includes determining a time-of-flight (TOF) information of at least a portion of the annihilations detected along a line of response between corresponding coincidence detectors and generating an image of the patient from the emission data using the determined TOF information.

81 Claims, 4 Drawing Sheets

METHOD AND SYSTEM FOR IMAGING A PATIENT

BACKGROUND OF THE INVENTION

The invention relates generally to medical imaging systems, and more particularly, to Positron Emission Tomography (PET) scanners.

PET scanners typically generate images depicting the distribution of positron-emitting nuclides in patients. The positron interacts with an electron in the body of the patient by annihilation, and then the electron-positron pair is converted into two photons. The photons are emitted in opposite directions along a line of response. The annihilation photons are detected by detectors that are placed on both sides of the line of response on the detector ring. The image is then generated based on the acquired emission data that includes the annihilation photon detection information.

In PET scanners the image quality depends on the image statistics. The image statistics may be improved by acquiring the emission data for longer durations. However, the total time of acquiring the emission data is limited by the decay of radioactive isotope and by the inability of the patients to lie still for extended durations.

Further, the image quality may be improved by including time-of-flight (TOF) information for the emission data. The TOF information is the time difference in detection of annihilation photon pair. The TOF is proportional to a position of origin of the annihilation photon pair along the line of response between corresponding coincidence detectors. The emission data is stored in a frame to include TOF information. However, when the emission data is stored in a frame, the memory and/or storage requirements increase significantly.

BRIEF DESCRIPTION OF THE INVENTION

In one exemplary embodiment, a method for imaging a patient is provided. The method includes determining a location of a volume of interest within the patient and acquiring a plurality of frames of emission data, at least one frame including the volume of interest. The method further includes determining a time-of-flight (TOF) information of at least a portion of annihilations detected along a line of response between corresponding coincidence detectors and generating an image of the patient from the emission data using the determined TOF information.

In another exemplary embodiment, a medical imaging system is provided. The medical imaging system includes a plurality of detectors configured to detect annihilation photons, a patient table configured to support a patient within a viewing area defined by the plurality of detectors and a patient table controller configured to control an axial position of the patient table within the viewing area. The medical imaging system further includes a computer communicatively coupled to at least one of the plurality of detectors and the patient table controller. The computer is programmed to, for a plurality of annihilation events, receive signals from the plurality of detectors of emission frames of data, the received signals define a line between two of the plurality of detectors that each detect an annihilation photon within a predetermined time window. The computer is further programmed to determine a time difference between the annihilation photons detection by each of the two detectors wherein the time difference is proportional to a position of an annihilation event along the defined line and to determine a volume of interest from a transmission scan. The computer is further programmed to generate an image using the determined time difference range.

DETAILED DESCRIPTION OF THE INVENTION

Various embodiments of the invention provide a method and system for imaging a patient using a medical imaging system. The medical imaging system may be, for example, a Positron Emission Tomography (PET) scanner, and/or a PET/Computed Tomography (CT) dual modality scanner.

Figure 1:
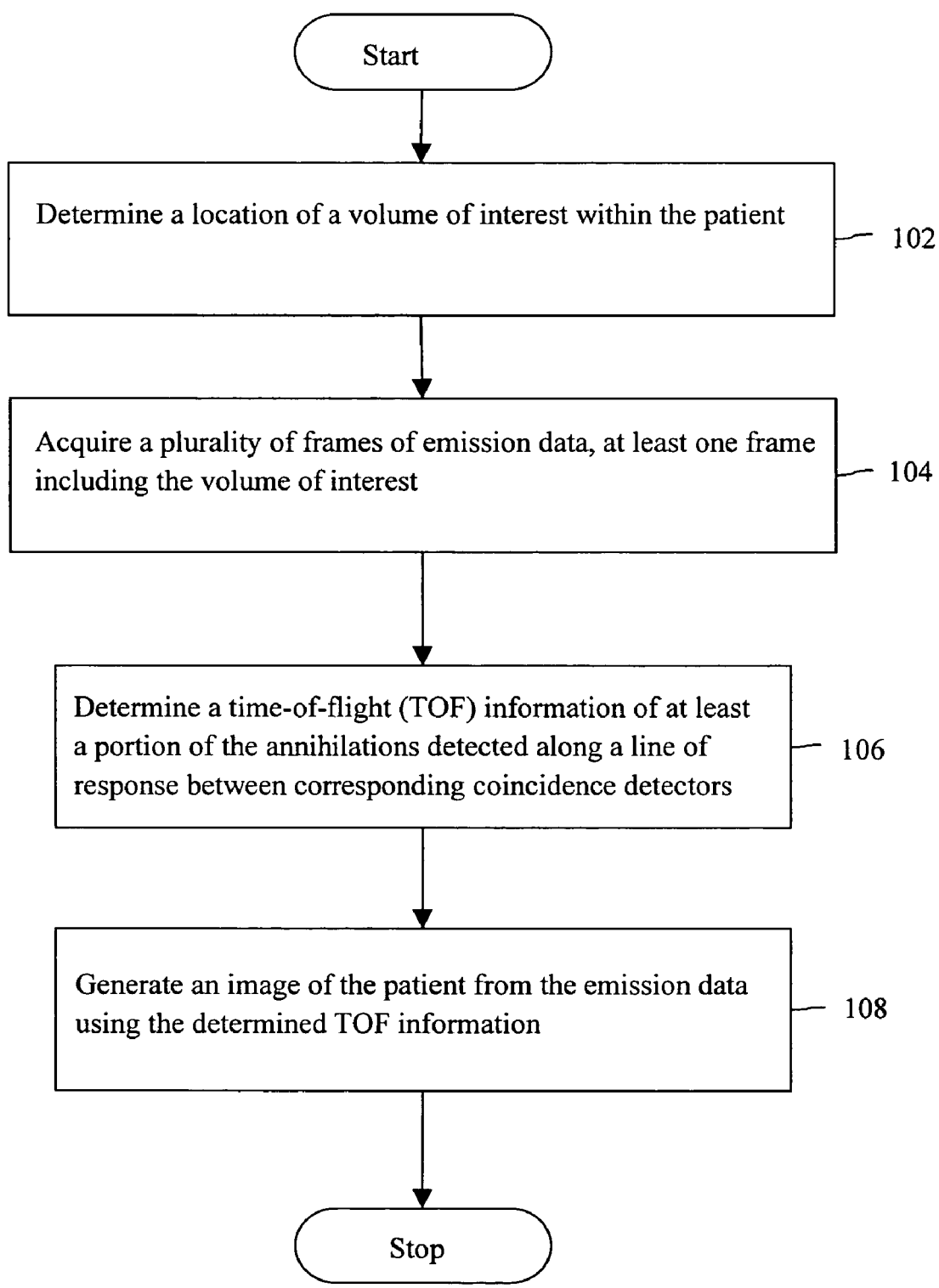
FIG. 1 is a flowchart illustrating a method for imaging a patient in accordance with an exemplary embodiment of the invention.

FIG. 1 is a flowchart illustrating a method for imaging a patient in accordance with an exemplary embodiment of the invention. At 102, a location of volume of interest within the patient is determined. In various embodiments of the invention, the volume of interest may be a particular region of the body of the patient, for example, an organ, a lesion, a nodule, a body part, etc. The volume of interest may be identified for imaging the particular region of the body of the patient for longer durations. The volume of interest may further be identified for selectively storing annihilation events.

In various embodiments of the invention, a volume of interest is determined, by localizing the volume of interest using a transmission data. In an embodiment of the invention, a CT scan may be performed to acquire the transmission data. In another embodiment of the invention, a PET transmission scan may be performed to acquire the transmission data. The PET transmission scan may be performed using a transmission scan feature of a PET scanner. In yet another embodiment, a CT scout scan is performed to acquire the transmission data. The CT scout scan may be performed using a scout scan feature of a CT scanner. An image is then generated based on the acquired transmission data. The volume of interest is localized automatically using computer-aided detection algorithms, such as Computer Aided Diagnosis (CAD) algorithms as described in U.S. Pat. No. 6,574,304, entitled "Computer aided acquisition of medical images", and U.S. Pat. No. 6,687,329, entitled "Computer aided acquisition of medical images", the entire disclosure of which is hereby incorporated by reference herein. In various embodiments of the invention, the volume of interest is identified manually by the user of medical imaging system. In yet another embodiment, a location of a volume of interest within the patient is determined by performing at least one of a PET transmission scan and a CT scout scan of the patient and automatically determining the volume of interest by comparing the scan data to a predetermined feature of historical scan data.

At 104, a plurality of frames of emission data of a patient is acquired using the medical imaging system, such that at least one frame includes the volume of interest. The emission data includes information from detected annihilation photons.

In various embodiments of the invention, a portion of the emission data may be acquired in a list mode. Further, another portion of the emission data may be acquired in a sinogram mode. The list mode generally refers to an acquisition mode in which each annihilation event is stored sequentially in a list mode file. The sinogram mode generally refers to an acquisition mode in which annihilation events having identical TOF are stored in sinograms. In an embodiment of the invention, a portion of the emission data may be acquired in the list mode for regions outside the volume of interest and a portion of emission data is acquired in the sinogram mode for the volume of interest. In another embodiment of the invention, a portion of the emission data may be acquired in the list mode for regions outside the volume of interest. Further, a portion of the emission data may be acquired simultaneously both in list mode and sinogram mode for the volume of interest. In yet another embodiment of the invention, a portion of the emission data may be acquired in the list mode for every x annihilation event, where x is a positive number greater than one. For example, for regions outside the volume of interest, x may be greater than one and for regions within the volume of interest x may be equal to one to ensure that each annihilation event with the volume of interest may be stored. In another embodiment of the invention, emission data may be acquired in the list mode for the entire field of view, simultaneously with emission data in the sinogram mode for the volume of interest for scatter correction.

In various embodiments of the invention, acquiring a plurality of frames of emission data includes storing a predetermined selectable portion of emission data in the list mode for determining a scatter correction.

In various embodiments of the invention, the volume of interest is moved from a first position corresponding to a frame that includes a first axial periphery of the volume of interest to a second position corresponding to a frame that includes a second axial periphery of the volume of interest. This ensures that the plurality of frames include the volume of interest when the volume of interest is axially longer than a field of view of the medical imaging system. For example, typical PET scanners have an axial field of view of 15 cm.

At 106, time-of-flight (TOF) information of at least a portion of the annihilation photons detected along a line of response (between corresponding coincidence detectors) is determined. In various embodiments of the invention, the line of response passes through the volume of interest. The TOF information is the time difference in detection of annihilation photon pair. The TOF information is proportional to a position of the origin of the annihilation photon pair along the line of response. The emission data is stored in a frame to include TOF information. An image of the patient is then generated based on the emission data using the TOF information of the emission data at 108. In various embodiments of the invention, the image is generated based on the emission data acquired in the list mode, the emission data acquired in the sinogram mode and the TOF information of the emission data. In another embodiment of the invention, an image may be generated based on the stored scatter correction data. In various embodiments of the invention, the acquired plurality of frames of the emission data may be used to perform kinetic modeling. The kinetic modeling generally refers to determining kinetic parameters relating to activity in the volume of interest.

In various embodiments of the invention, a PET scan protocol is determined based on at least one of attenuation data from the transmission data and the location of the volume of interest. For example, while acquiring the transmission scan, the user observes comparatively higher attenuation in some regions within the volume of interest. The user may then determine a PET scan protocol such that the acquisition time for the comparatively higher attenuating regions within the volume of interest is higher. In an embodiment of the invention, a PET scan protocol is determined by determining acquisition time for each of the plurality of frames of emission data using the attenuation data. In an embodiment of the invention, a PET scan protocol is determined by determining acquisition time for each of the plurality of frames of emission data wherein the acquisition time for frames that include the volume of interest is greater than the acquisition time for frames outside the volume of interest. In yet another embodiment of the invention, a PET scan protocol is determined by determining an order of acquiring the plurality of frames of emission data based on a radioactive decay of a radiopharmaceutical administered to the patient. In an embodiment of the invention, since the activity of the radiopharmaceutical administered to the patient decreases with the radioactive decay, a portion of frames of emission data that include the volume of interest may be acquired first. In another embodiment of the invention, a PET scan protocol is determined by determining the acquisition time for each frame of emission data based on a radioactive decay of a radiopharmaceutical administered to the patient. For example, the acquisition time for a volume of interest may be higher when the activity of the radiopharmaceutical administered to the patient is low.

Figure 2:
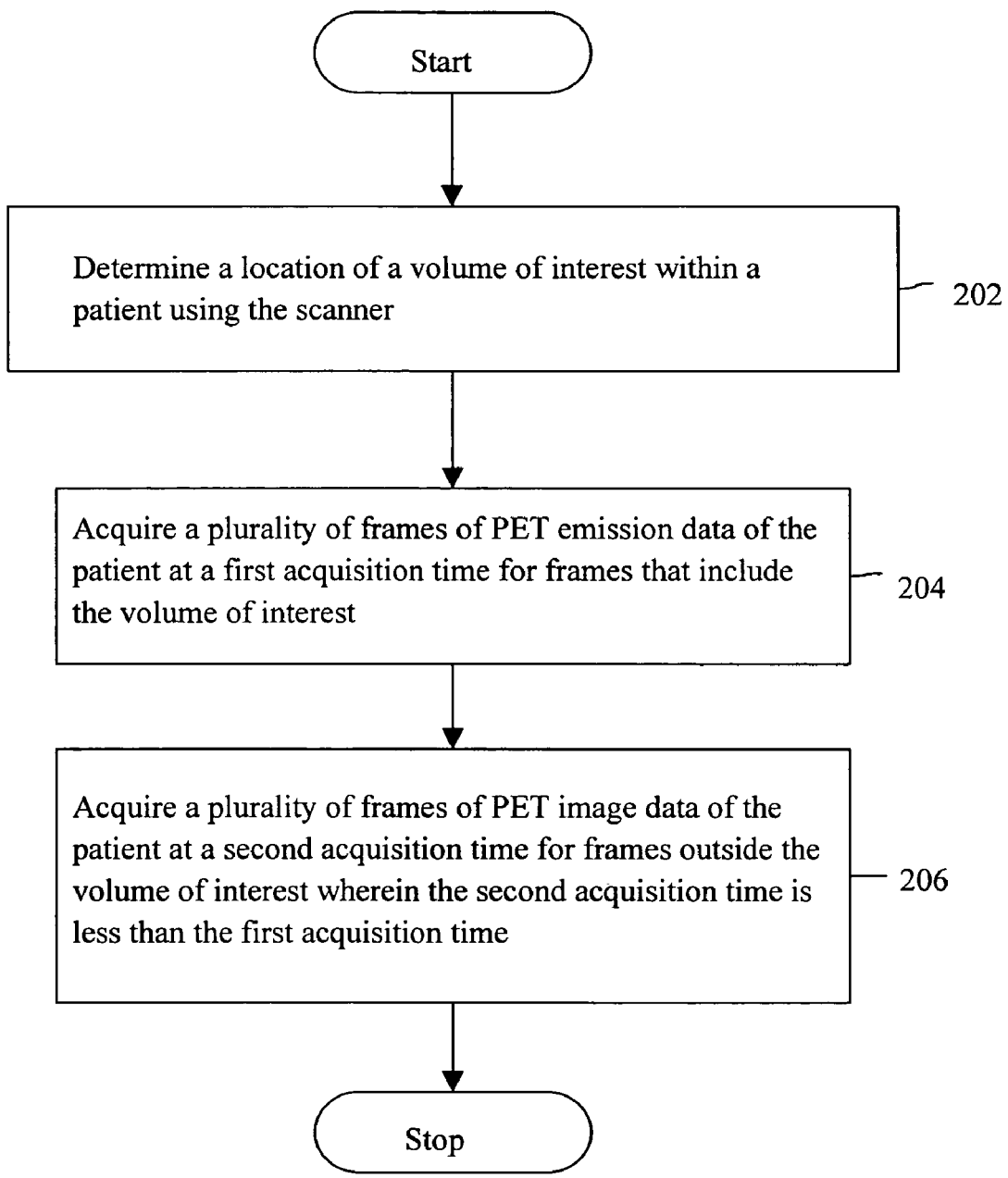
FIG. 2 is a flowchart illustrating a method for imaging a patient in accordance with another embodiment of the invention.

FIG. 2 is a flowchart illustrating a method for imaging a patient in accordance with another embodiment of the invention. At 202, a volume of interest is determined within a patient a scanner. In an embodiment of the invention, a CT scan is performed to determine the volume of interest. In another embodiment of the invention, a PET transmission scan is performed to determine the volume of interest. The PET transmission scan may be performed using a transmission scan feature of a PET scanner. In various embodiments of the invention, the volume of interest may be a particular region of the body of the patient, for example, an organ, a lesion, a nodule, a body part, etc. The medical imaging system then acquires a plurality of frames of emission data of a patient at a first acquisition time such that the plurality of frames include a volume of interest at 204. The emission data is a PET emission data. Further, the medical imaging system acquires a plurality of frames of emission data of a patient for frames outside the volume of interest at a second acquisition time, the second acquisition time being less than the first acquisition time, at 206. In an embodiment of the invention, the medical imaging system may be a PET/CT dual modality scanner.

In various embodiments of the invention, the medical imaging system acquires a plurality of frames for emission data corresponding to annihilation photon pairs that have the time difference within a predetermined window. The predetermined time window is described in conjunction with FIG. 4.

Figure 3:
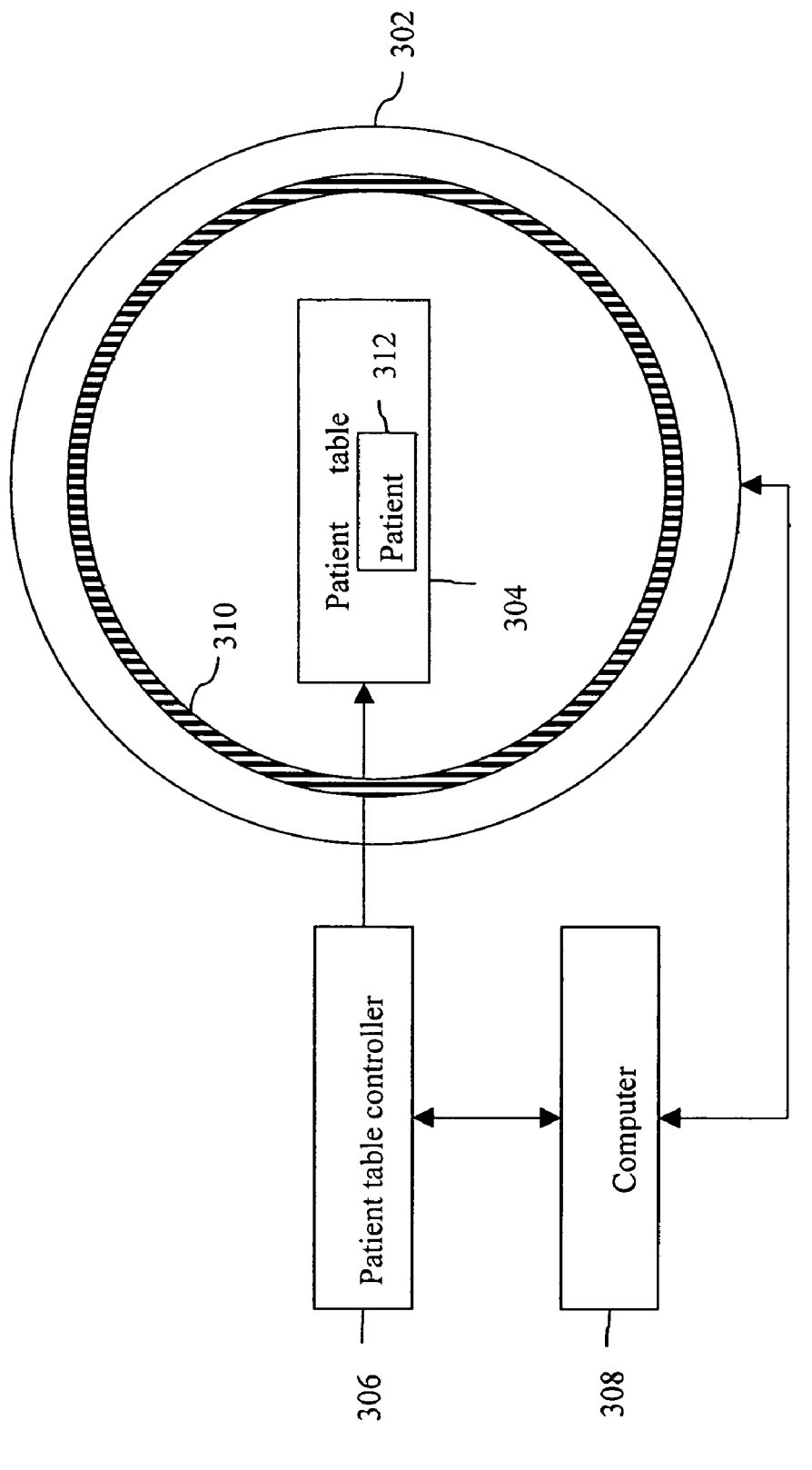
FIG. 3 is a block diagram of a medical imaging system in accordance with an exemplary embodiment of the invention.

FIG. 3 is a block diagram of a medical imaging system 300 in accordance with an exemplary embodiment of the invention. Medical imaging system 300 includes a detector ring 302, a patient table 304, a patient table controller 306, and a computer 308.

Detector ring 302 includes a plurality of detectors 310. Detectors typically include radiation detectors with sufficiently high timing resolution. The high timing resolution may be required to discriminate between at least two positions along the line of response joining two such detectors. The photons are emitted in opposite direction along a line of response and are simultaneously detected by detectors 310 placed on the line of response.

Patient table 304 is configured to support a patient 312 within an axial field of view. Patient table controller 306 is configured to control an axial position of patient table 304 within the axial field of view.

Computer 308 is communicatively coupled to detector ring 302, more specifically, to one of the plurality of detectors 310 and patient table controller 306. In various embodiments of the invention, computer 308 controls medical imaging system 300 to acquire the transmission data and determine a volume of interest based on the transmission data. In an embodiment of the invention, computer 308 controls medical imaging system 300 to perform at least one of CT scan, PET transmission scan, and a CT scout scan to acquire the transmission data. In various embodiments of the invention, computer 308 is programmed to automatically move a volume of interest from a first position corresponding to a frame that includes a first axial periphery of the volume of interest to a second position corresponding to a frame that includes a second axial periphery of the volume of interest. In an embodiment of the invention, computer 308 moves the volume of interest in response to a user input. In another embodiment of the invention, computer 308 automatically moves the volume of interest based on the transmission data.

In various embodiments of the invention, computer 308 is programmed to modulate the time spent at a particular location of patient table 304. This enables a user of medical imaging system 300 increase the acquisition time of a particular region of the body.

Computer 308 is programmed to determine a volume of interest. Further, computer 308 is programmed to receive signals from detector ring 302 for a plurality of frames of emission data. Computer 308 is further programmed to determine TOF information between the annihilation photons detection by each of the two detectors 310 and to generate the image based on the received signals using the determined TOF information.

In various embodiments of the invention, computer 308 is programmed to acquire emission data in the list mode and sinogram mode and generate the image based on the emission data acquired in the list mode, the emission data acquired in the sinogram mode and the TOF information of the emission data.

In various embodiments of the invention, computer 308 is programmed to receive signals from detector ring 302 for emission data corresponding to annihilation photon pairs that have the TOF information within a predetermined window. The predetermined time window is described in conjunction with FIG. 4.

In various embodiments of the invention, computer 308 is programmed to perform the method described in conjunction with FIG. 1. In another embodiment of the invention, computer 308 is programmed to perform the method described in conjunction with FIG. 2.

Figure 4:
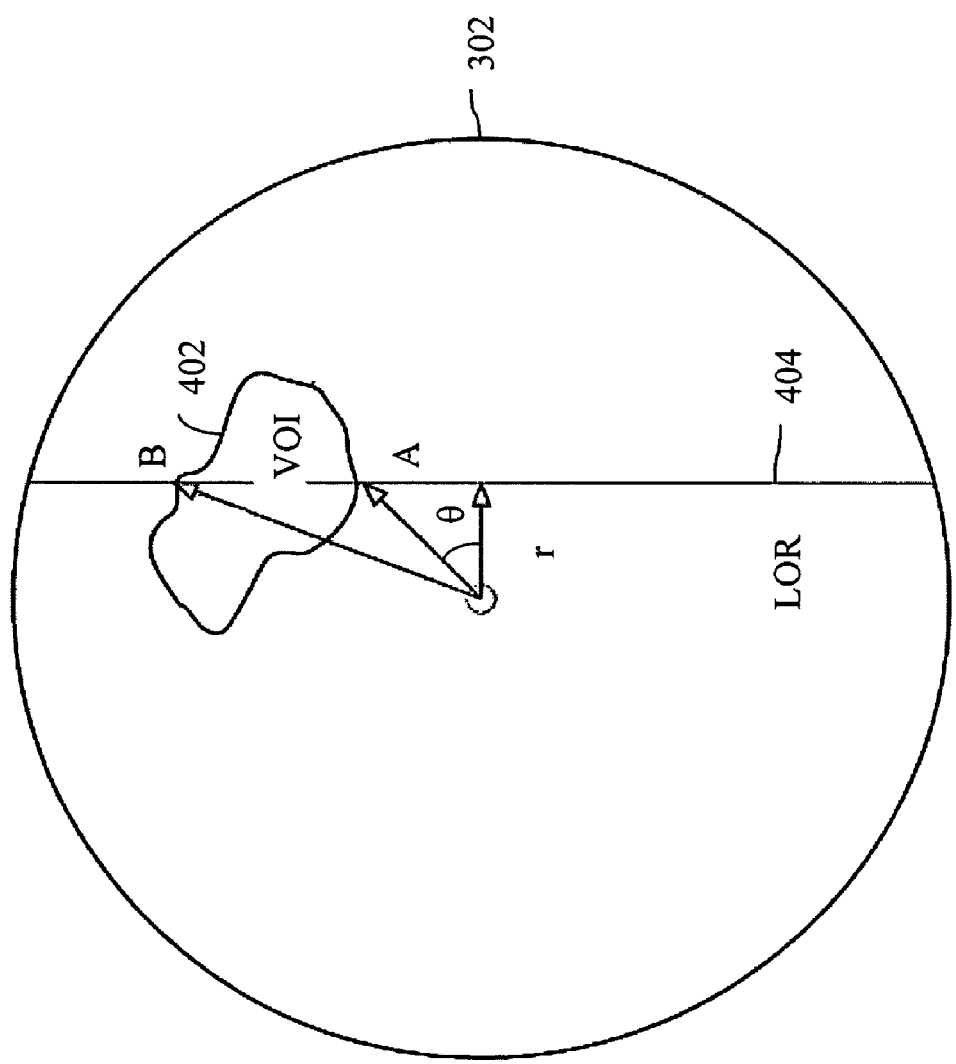
FIG. 4 is an illustration of a method for imaging a patient in accordance with an exemplary embodiment of the invention.

FIG. 4 is an illustration of a method for imaging a patient in accordance with an exemplary embodiment of the invention. In various embodiments of the invention, annihilation photons with TOF information within a predetermined time window are acquired. This further reduces the memory and/or the storage requirements of the emission data. The TOF information may be used to determine the position of the origin of the annihilation photon pair along the line of response. In various embodiments of the invention, the TOF information should satisfy the following equation (1):

$$(T_{diff}*c/2) < (x,y,z)_{volume\ of\ interest} or (r,\theta,\phi)_{volume\ of\ interest} \quad (1)$$

where,
$T_{diff}$ is the TOF information of an annihilation photon pair;
c is speed of light;
$(x,y,z)$ or $(r,\theta,\phi)$ defines the spatial location of a volume of interest 402;

In various embodiments of the invention, the predetermined time window includes the values of TOF information satisfying equation (1). For example, the TOF information of annihilation photons emitted from points between A and B on volume of interest 402 along a line of response 404 satisfies equation (1). Alternatively, the TOF information of annihilation photons emitted from points between A and B may satisfy the following equation (2):

$$(\text{round}(D_{min}/D_{tof})+1) < (T_{diff}*c/2) < (\text{round}(D_{max}/D_{tof})+1) \quad (2)$$

where,
$D_{min}$ is $(T_{diff}$ at point A$)*c/2$;
$D_{tof}$ is $(T_{sample})*c/2$;
$D_{max}$ is $(T_{diff}$ at point B$)*c/2$; and
round( ) operator refers to the nearest integer function.

In various embodiments of the invention, $T_{sample}$ may be timing Least Significant Bit (LSB) of detector ring 302. For example, in a PET scanner if the timing difference is measured in 250 ps increments (i.e. timing LSB is 250 ps), then $T_{sample}$ may be 250 ps.

In various embodiments of the invention, additional number of $T_{diff}$ are included to eliminate 'edge effects' of volume of interest 402. In various embodiments of the invention, the range of the predetermined time window is increased by one. This is further illustrated in equation (2).

In various embodiments of the invention, a sinogram is generated for annihilation photon pairs corresponding to TOF within the predetermined time window. The sinograms are then populated with respective TOF emission data during the emission scan. Further, an image is generated based on the generated sinograms.

In various embodiments of the invention, the predetermined time window may be selected such that the emission data may be acquired for annihilation events occurring within volume of interest 402 for a first selectable acquisition time. Further, the predetermined time window may be selected such that the emission data may be acquired for annihilation events occurring external to volume of interest 402 for a second selectable acquisition time, wherein the second selectable acquisition time is different from the first selectable acquisition time. Further, the predetermined time window may be selected such that the emission data is acquired for annihilation events occurring adjacent to volume of interest 402 for a third selectable acquisition time, wherein the third selectable acquisition time is different from the second selectable acquisition time.

In various embodiments of the invention, information from a CT scan may be used for attenuation correction and fusion display. Further, in various embodiments of the invention, an identified lesion within volume of interest 402 is characterized using the transmission data. The characterizing of the identified lesion generally refers to determining at least one of the lesion size, shape, density, and orientation with respect to volume of interest 402. In an embodiment of the invention, a CT scan may be performed to acquire the transmission data. In another embodiment of the invention, a PET transmission scan may be performed to acquire the transmission data.

The acquisition time of emission data (using medical imaging system 300) is generally for over a period of several minutes. During the acquisition, patients breathe normally and therefore, any object for example, within in or near the lungs is subject to motion. This motion translates into a spatial 'smearing' of at least one of the detected of the annihilation events, which decreases the computed value of the resulting Significant Uptake Value (SUV). However, a CT scan is acquired quickly while the patient is in breath hold. Therefore, the CT scan may be used for corrections in the SUV of the emission data. The specific uptake value generally refers to ratio of a decay corrected activity concentration at volume of interest 402 to the activity injected per unit mass of the patient.

In various embodiments of the invention, SUVs of the emission data may be corrected for lesion density using the characterization of the lesion. A hypothetical three dimensional distribution of activity is assigned to volume of interest 402. For example, a simple homogenous activity concentration may be activity distributed throughout the lesion within volume of interest 402. Thereafter, the generated image and the hypothetical activity distribution may be used to generate a set of correction coefficients that may be applied to the lesion (either in sinogram space, image space, or in the process of reconstruction) in the generated image in order to reduce the bias in the estimate of activity concentration (and consequently SUV).

In another embodiment of the invention, the SUVs of the emission data may be corrected for scanner point spread function using the characterization of the lesion. In yet another embodiment of the invention, the SUV of the emission data may be corrected for patient motion using the characterization.

The various embodiments of the invention provide a medical imaging system that enables imaging of a volume of interest. Further, the various embodiments of the invention provide a medical imaging system that enables reduction in the memory and/or the storage required for emission data and the maximum data rate that needs to be histogrammed or saved in list mode.

The various embodiments of the invention provide a medical imaging system that enables the determination of the axial extent of imaging (i.e. the start/stop location of the patient table required to include a volume of interest). This may facilitate performing cardiac studies where it is essential to include the volume of interest, i.e. the heart, in the field of view in a single patient table position.

The various embodiments of the invention provide a medical imaging system that enables modulation of time spent at a particular axial location.

A technical effect of the various embodiments of the invention is to enable imaging of a volume of interest. Another technical effect of the invention is to reduce the memory and/or storage required for the emission data and the maximum data rate that needs to be histogram or saved in list mode. Yet another technical effect of the invention is to enable determination of the axial extent of imaging. Another technical effect of the invention is to enable modulation of time spent at a particular axial location.

The various embodiments or components thereof may be implemented as part of a computer system. The computer system may include a computer, an input device, a display unit and an interface, for example, for accessing the Internet. The computer may include a microprocessor. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into the computer system.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer system executes a set of instructions that are stored in one or more storage elements, in order to process input data. The storage elements may also hold data or other information as desired or needed. The storage element may be in the form of an information source or a physical memory element within the processing machine.

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While the invention has been described in terms of various specific embodiments, those skilled in the art will recognize that the invention can be practiced with modification within the spirit and scope of the claims.

What is claimed is:

1. A method of imaging a patient using a positron emission tomography (PET)/computed tomography (CT) dual modality scanner, said method comprising:

determining a location of a volume of interest within the patient;

determining a predetermined time window associated with the volume of interest;

acquiring a plurality of frames of emission data, at least one frame including the volume of interest;

automatically moving the volume of interest from a first position corresponding to a frame that includes a first axial periphery of the volume of interest to a second position corresponding to a frame that includes a second axial periphery of the volume of interest;

determining a time-of-flight (TOF) information of at least a portion of the annihilations detected along a line of response between corresponding coincidence detectors;

rejecting TOF information that is greater than the predetermined time window associated with the volume of interest; and generating an image of the patient from the emission data using the determined TOF information.

2. A method in accordance with claim 1 wherein determining a location of a volume of interest within the patient comprises localizing the volume of interest using transmission data.

3. A method in accordance with claim 2 wherein localizing the volume of interest using transmission data comprises:
generating computed tomography (CT) images from the transmission data;
automatically localizing the volume of interest using computer-aided detection algorithms on the CT images.

4. A method in accordance with claim 3 further comprising determining a positron emission tomography (PET) scan protocol based on at least one of attenuation data from the transmission data and the location of the volume of interest.

5. A method in accordance with claim 4 wherein determining a positron emission tomography (PET) scan protocol comprises determining a duration of data acquisition for each of the plurality of frames of emission data using the attenuation data.

6. A method in accordance with claim 4 wherein determining a positron emission tomography (PET) scan protocol comprises determining a duration of data acquisition for each of the plurality of frames of emission data wherein the duration for frames that include the volume of interest is greater than the duration for frames outside the volume of interest.

7. A method in accordance with claim 4 wherein determining a positron emission tomography (PET) scan protocol comprises determining an order of acquiring the plurality of frames of emission data using a radioactive decay of a radiopharmaceutical administered to the patient.

8. A method in accordance with claim 7 wherein determining an order of acquiring the plurality of frames of emission data comprises first acquiring emission data from a portion of the plurality of frames of emission data that include the volume of interest and then acquiring emission data from a portion of the plurality of frames of emission data that is outside the volume of interest.

9. A method in accordance with claim 4 wherein determining a positron emission tomography (PET) scan protocol comprises determining an acquisition duration for each frame of emission data using a radioactive decay of a radiopharmaceutical administered to the patient.

10. A method in accordance with claim 2 further comprising characterizing an identified lesion in the volume of interest using the transmission data.

11. A method in accordance with claim 10 wherein characterizing an identified lesion in the volume of interest comprises determining at least one of the lesion size, shape, density, and orientation with respect to the volume of interest.

12. A method in accordance with claim 11 further comprising correcting Significant Uptake Values (SUVs) of the emission data for lesion density using the characterization.

13. A method in accordance with claim 11 further comprising correcting Significant Uptake Values (SUVs) of the emission data for scanner point spread using the characterization.

14. A method in accordance with claim 11 further comprising correcting Significant Uptake Values (SUVs) of the emission data for patient motion using the characterization.

15. A method in accordance with claim 10 further comprising:
characterizing the lesion using emission data from a PET scan; and
combining the characterization using the transmission data with the characterization using the emission data such that a determination of malignancy and staging is facilitated.

16. A method in accordance with claim 1 wherein determining a location of a volume of interest within the patient comprises localizing the volume of interest using emission data.

17. A method in accordance with claim 16 wherein localizing the volume of interest using emission data comprises conducting a positron emission tomography (PET) transmission scan of the patient.

18. A method in accordance with claim 1 further comprising attenuation correcting the image using information from a CT scan.

19. A method in accordance with claim 1 wherein acquiring a plurality of frames of emission data comprises:
selecting a time range for TOF difference along the line of response;
generating a sinogram for each selected time difference range; and
populating the sinogram with respective TOF emission data during the emission scan.

20. A method in accordance with claim 19 further comprising acquiring emission data for TOF time ranges corresponding to annihilations occurring within the volume of interest for a first selectable time period.

21. A method in accordance with claim 20 further comprising acquiring emission data for TOF time ranges corresponding to annihilations occurring external to the volume of interest for a second selectable time period wherein the second time period is different than the first time period.

22. A method in accordance with claim 21 further comprising acquiring emission data for TOF time ranges corresponding to annihilations occurring adjacent to the volume of interest for a third selectable time period wherein the third time period is different from the first time period and different from the second time period.

23. A method in accordance with claim 1 wherein generating an image of the patient comprises reconstructing the image using a plurality of sinograms, each sinogram including frame data for a single coincident gamma ray detection time range.

24. A method in accordance with claim 1 further comprising:
acquiring a portion of the emission data from a frame in a list mode;
acquiring a portion of the emission data from the frame in a frame mode; and
wherein generating an image of the patient comprises reconstructing the image using data from the list mode and a plurality of sinograms, each sinogram including frame data for a single coincident gamma ray detection time range.

25. A method in accordance with claim 1 wherein acquiring a plurality of frames of emission data comprises storing a predetermined selectable portion of the emission data in list mode for determining a scatter correction.

26. A method in accordance with claim 25 wherein generating an image of the patient further comprising generating an image of the patient using the stored scatter correction data.

27. A method of imaging a patient, said method comprising:
performing a PET transmission scan of a patient;
acquiring a plurality of frames of emission data, at least one frame including the volume of interest;
automatically determining a location of at least one volume of interest in the patient by comparing the scan data to at least one predetermined feature of historical scan data acquired by imaging the patient;

determining a time-of-flight (TOF) information of at least a portion of the annihilations detected along a line of response between corresponding coincidence detectors; and generating an image of the patient from the emission data using the determined TOF information.

28. A method for medical image scanning using a positron emission tomography (PET) scanner, the method comprising:
determining a location of a volume of interest within a patient using the scanner;
acquiring a plurality of frames of PET emission data of the patient at a first acquisition time for frames that include the volume of interest; and
acquiring a plurality of frames of PET emission data of the patient at a second acquisition time for frames outside the volume of interest, wherein the second acquisition time is less than the first acquisition time.

29. A method in accordance with claim 28 wherein determining a volume of interest comprises performing a CT scan determine the volume of interest.

30. A method in accordance with claim 28 wherein determining a location of a volume of interest comprises performing at least one of a PET transmission scan and a CT scout scan to determine the volume of interest.

31. A method in accordance with claim 30 wherein performing a scout scan to determine a volume of interest comprises performing a transmission scout scan to determine the volume of interest.

32. A method in accordance with claim 30 wherein performing a scout scan to determine a volume of interest comprises performing a PET transmission scan to determine the volume of interest.

33. A method in accordance with claim 28 further comprising determining an attenuation correction and fusion display of the PET image using information from a CT scan.

34. A method in accordance with claim 28 wherein scanning the patient to determine a volume of interest comprises scanning the patient to automatically determine at least one of an organ, a lesion, a nodule, and a body part.

35. A medical imaging system comprising:
a plurality of detectors configured to detect annihilation photons;
a patient table configured to support a patient within a viewing area defined by the plurality of detectors;
a patient table controller configured to control an axial position of the patient table within the viewing area, and
a computer communicatively coupled to at least one of the plurality of detectors and the patient table controller, said computer programmed to, for a plurality of annihilation events:
determine a volume of interest from a transmission scan;
acquire a plurality of frames of emission data at a first acquisition time and a second acquisition time where the second acquisition time is less than the first acquisition time, at least one frame including the volume of interest;
receive signals from the plurality of detectors for a plurality of emission frames of data, the received signals define a line of response between two of the plurality of detectors that each detect an annihilation photon within a predetermined time window;
determine a time difference between the annihilation photons detection by each of the two detectors wherein the time difference is proportional to a position of an annihilation event along the defined line; and
generate an image using the determined time difference.

36. A medical imaging system in accordance with claim 35 comprising a computed tomography scanner.

37. A medical imaging system in accordance with claim 35 comprising a positron emission tomography (PET) scanner.

38. A medical imaging system in accordance with claim 35 wherein said computer is further programmed to determine a volume of interest from at least one of a PET transmission scan and a CT scout scan.

39. A medical imaging system in accordance with claim 35 wherein said computer is further programmed to use information from a CT scan for attenuation correction and fusion display of the PET image.

40. A medical imaging system in accordance with claim 35 wherein said computer is further programmed to automatically move a volume of interest from a first position corresponding to a frame that includes a first axial periphery of the volume of interest to a second position corresponding to a frame that includes a second axial periphery of the volume of interest using the patient table controller.

41. A medical imaging system in accordance with claim 35 wherein said computer is further programmed to localize the volume of interest using transmission data.

42. A medical imaging system in accordance with claim 41 wherein said computer is further programmed to:
generate computed tomography (CT) images from the transmission data;
automatically localize the volume of interest using computer-aided detection algorithms on the CT images.

43. A medical imaging system in accordance with claim 42 wherein said computer is further programmed to determine a positron emission tomography (PET) scan protocol based on at least one of attenuation data from the transmission data and the location of the volume of interest.

44. A medical imaging system in accordance with claim 43 wherein said computer is further programmed to determine a duration of data acquisition for each of the plurality of frames of emission data using the attenuation data.

45. A medical imaging system in accordance with claim 43 wherein said computer is further programmed to determine a duration of data acquisition for each of the plurality of frames of emission data wherein the duration for frames that include the volume of interest is greater than the duration for frames outside the volume of interest.

46. A medical imaging system in accordance with claim 43 wherein said computer is further programmed to determine an order of acquiring the plurality of frames of emission data using a radioactive decay of a radiopharmaceutical administered to the patient.

47. A medical imaging system in accordance with claim 46 wherein said computer is further programmed to first acquire emission data from a portion of the plurality of frames of emission data that includes the volume of interest and then acquiring emission data from a portion of the plurality of frames of emission data that is outside the volume of interest.

48. A medical imaging system in accordance with claim 43 wherein said computer is further programmed to determine acquisition duration for each frame of emission data using a radioactive decay of a radiopharmaceutical administered to the patient.

49. A medical imaging system in accordance with claim 43 wherein said computer is further programmed to localize the volume of interest using emission data.

50. A medical imaging system in accordance with claim 49 wherein said computer is further programmed to conduct a positron emission tomography (PET) transmission scan of the patient.

51. A medical imaging system in accordance with claim 35 wherein said computer is further programmed to attenuation correct the image using information from a CT scan.

52. A medical imaging system in accordance with claim 35 wherein said computer is further programmed to:
perform at least one of a PET transmission scan and a CT scout scan of the patient; and
automatically determine at least one volume of interest by comparing the scan data to at least one predetermined feature of historical scan data.

53. A medical imaging system in accordance with claim 35 wherein said computer is further programmed to automatically move the volume of interest from a first position corresponding to an emission frame that includes a first axial periphery of the volume of interest to a second position corresponding to an emission frame that includes a second axial periphery of the volume of interest.

54. A medical imaging system in accordance with claim 35 wherein said computer is further programmed to:
select a time range for TOF difference along the line of response;
generate a sinogram for each selected time difference range; and
populate the sinograms with respective TOF emission data during the emission scan.

55. A medical imaging system in accordance with claim 54 wherein said computer is further programmed to acquire emission data for TOF time ranges corresponding to annihilations occurring within the volume of interest for a first selectable time period.

56. A medical imaging system in accordance with claim 55 wherein said computer is further programmed to acquire emission data for TOF time ranges corresponding to annihilations occurring external to the volume of interest for a second selectable time period wherein the second time period is different than the first time period.

57. A medical imaging system in accordance with claim 56 wherein said computer is further programmed to acquire emission data for TOF time ranges corresponding to annihilations occurring adjacent to the volume of interest for a third selectable time period wherein the third time period is different from the first time period and different from the second time period.

58. A medical imaging system in accordance with claim 35 wherein said computer is further programmed to reconstruct the image using a plurality of sinograms, each sinogram including frame data for a single coincident gamma ray detection time range.

59. A medical imaging system in accordance with claim 35 wherein said computer is further programmed to:
acquire a portion of the emission data from a frame in a list mode;
acquire a portion of the emission data from the frame in a sinogram mode; and
reconstruct the image using data from the list mode and a plurality of sinograms, each sinogram including frame data for a single coincident gamma ray detection time range.

60. A medical imaging system in accordance with claim 35 wherein said computer is further programmed to store a predetermined selectable portion of the emission data in list mode for determining a scatter correction.

61. A medical imaging system in accordance with claim 60 wherein said computer is further programmed to generating an image of the patient using the stored scatter correction data.

62. A method of imaging a patient using a positron emission tomography (PET)/computed tomography (CT) dual modality scanner, the method comprising:
performing a list mode acquisition of emission data for at least a portion of a volume of interest to form a list mode data set;
performing a sinogram mode of acquisition of emission data for at least a portion of the volume of interest to from a sinogram mode data set, wherein the acquisitions of emission data in list mode and sinogram mode are performed simultaneously; and
generating an image of the patient from at least a portion of at least one of the list mode and sinogram mode data sets.

63. The method of claim 62, wherein the emission data acquired in list mode includes emission data for every X annihilation event where X is a positive number greater than one.

64. The method of claim 62, wherein the emission data is acquired in list mode for a field of view including an area outside of the volume of interest, while the emission data acquired in sinogram mode is only acquired for the volume of interest, not outside the volume of interest.

65. The method of claim 62, further comprising performing scatter correction based on the emission data acquired in list mode.

66. The method of claim 62, further comprising determining kinetic parameters based on at least one of the list mode and sinogram mode data sets, the kinetic parameters relating to activity in the volume of interest.

67. The method of claim 66, wherein the kinetic parameters model activity in the volume of interest.

68. The method of claim 62, further comprising controlling an acquisition time for frames of emission data based on radio active decay of a radio pharmaceutical administered to a patient.

69. The method of claim 62, further comprising controlling an acquisition time for frames of emission data such that an acquisition time for the volume of interest is higher when activity of a radio pharmaceutical administered to a patient is low.

70. The method of claim 62, further comprising controlling an acquisition time for frames of emission data that include the volume of interest to be greater than an acquisition time for frames of emission data outside of the volume of interest.

71. The method of claim 62, further comprising displaying a fusion image comprising the image generated based on the emission data and a CT image based on CT data.

72. The method of claim 62, wherein the sinogram mode data set is acquired for a region without motion and the list mode data set is acquired for a region subject to motion.

73. A method of imaging a patient using a positron emission tomography (PET)/computed tomography (CT) dual modality scanner, the method comprising:
positioning a patient table at a first location relative to detectors for a first acquisition time;
acquiring emission data for a volume of interest while at the first location for the first acquisition time;
repositioning the patient table at a second location relative to the detectors for a second acquisition time;
acquiring emission data for a volume of interest while at the second location for the second acquisition time; and
generating an image based on the emission data acquired at the first and second locations.

74. The method of claim 73, further comprising modulating at least one of the first and second acquisition times in order to increase acquisition time of a particular region of the patient.

75. The method of claim 73, further comprising acquiring transmission data and determining the volume of interest based on the transmission data.

76. The method of claim 75, wherein the transmission data is acquired using one of a CT scan, a PET transmission scan and a scout scan.

77. The method of claim 73, further comprising modulating a time spent by the patient table at, at least one of the first and second locations based on motion within the volume of interest.

78. The method of claim 73, further comprising assigning a distribution of activity to the volume of interest.

79. The method of claim 73, further comprising assigning a single hypothetical activity concentration throughout a lesion within the volume of interest.

80. The method of claim 73, further comprising assigning an activity distribution to a lesion, and generating correction coefficients based on the activity distribution to apply to the lesion in the image generated to reduce bias in an estimate of activity concentration.

81. The method of claim 73, further comprising calculating a significant uptake value (SUV) based on the emission data, and correcting the SUV for patient motion.

* * * * *